United States Patent
Wang et al.

(10) Patent No.: US 11,512,120 B2
(45) Date of Patent: Nov. 29, 2022

(54) **ANTIMICROBIAL PEPTIDE SCYREPROCIN OF *SCYLLA PARAMAMOSAIN* AND METHOD THEREOF**

(71) Applicant: Xiamen University, Fujian (CN)

(72) Inventors: Kejian Wang, Fujian (CN); Ying Yang, Fujian (CN); Fangyi Chen, Fujian (CN); Yanchao Chen, Fujian (CN); Huiyun Chen, Fujian (CN); Hui Peng, Fujian (CN)

(73) Assignee: Xiamen University, Fujian (CN)

( * ) Notice: Subject to any disclaimer, the term of this patent is extended or adjusted under 35 U.S.C. 154(b) by 0 days.

(21) Appl. No.: 17/230,243

(22) Filed: Apr. 14, 2021

(65) Prior Publication Data

US 2021/0317172 A1   Oct. 14, 2021

Related U.S. Application Data

(63) Continuation of application No. PCT/CN2019/103237, filed on Aug. 29, 2019.

(30) Foreign Application Priority Data

Nov. 21, 2018 (CN) .......................... 201811394517.8

(51) Int. Cl.
  *C07K 14/435* (2006.01)
  *A23K 20/147* (2016.01)
  *A61P 31/10* (2006.01)
  *A61K 45/06* (2006.01)

(52) U.S. Cl.
  CPC ...... *C07K 14/43509* (2013.01); *A23K 20/147* (2016.05); *A61K 45/06* (2013.01); *A61P 31/10* (2018.01)

(58) Field of Classification Search
  CPC ............................................... C07K 14/43509
  See application file for complete search history.

(56) References Cited

FOREIGN PATENT DOCUMENTS

| CN | 102167736 A | 8/2011 |
| CN | 103789317 A | 5/2014 |
| CN | 104151414 A | 11/2014 |
| CN | 105274134 A | 1/2016 |
| WO | 2009019632 A1 | 2/2009 |

OTHER PUBLICATIONS

Schnaider et al., "Self-assembling dipeptide antibacterial nanostructures with membrane disrupting activity", Nature Communications, 2017, 10 pages (Year: 2017).*
Brondyk, "Chapter 11 Selecting an Appropriate Method for Expressing a Recombinant Protein", Methods of Enzymology, 2009, pp. 131-147 (Year: 2009).*
Gen Bank Accession No. QDA76506.1 (Year: 2020).*
Gen Bank Accession No. MH488960 (Year: 2020).*
International Search Report and English Translation of International Search Report as cited in PCT Application No. PCT/CN2019/103237, dated Nov. 28, 2019, 10 pages.
Written Opinion as cited in PCT Application No. PCT/CN2019/103237, dated Nov. 28, 2019, 4 pages.
Xu Wanfang, et al., "Recombinant Expression of the Anti-microbial Peptide, Scygonadin from Scylla Paramamosain in Pichia Pastoris and its Antimicrobial Activity", Journal of Quanzhou Normal University, vol. 29, Issue 6, Nov. 30, 2011 (Nov. 30, 2011), pp. 11-15, with English abstract.
Peng Yinhui et al., "Optimization of Prokaryotic Expression Conditions for the Antimicrobial Peptide Hyastatin Gene of Scylla sinensis", Biotechnology Bulletin, vol. 31, Issue 7, Dec. 31, 2015 (Dec. 31, 2015), pp. 138-142, with English abstract.
Shan, Zg, etc., "The New Antimicrobial Pepetide SpHyastatin from the Mud Crab *Scylla paramamosain* with Multiple Antimicrobial Mechanisms and High Effect on Bacterial Infection", Frontiers in Microbiology, vol. 7, Jul. 21, 2016 (Jul. 21, 2016), p. 1-14.
Imjongjirak, C., etc., "Two novel antimicrobial peptides, arasin-likeSp and GRPSp, from the mud crab *Scylla paramamosain*, exhibit the activity against some crustacean pathogenic bacteria", Fish & Shellfish Immunology, vol. 30, Jan. 8, 2011 (Jan. 8, 2011), pp. 706-712.
Qiao, et al., "A new antimicrobial peptide SCY2 identified in Scylla Paramamosain exerting a potential role of reproductive immunity", Feb. 18, 2016, 12 pages.
Notice of Allowance and English translation of CN 201811394517.8, dated Jul. 24, 2021, 3 pages.
First Office Action and English translation of CN 201811394517.8, dated Jun. 3, 2021, 4 pages.
Peng, et al., "Expression, purification and antimicrobial activity of SCY2 from mud crab *Scylla paramamosain* in yeast *Pichia pastoris*", http://www.cnki.net, vol. 33, No. 2, Apr. 2018, 7 pages.

* cited by examiner

*Primary Examiner* — Lianko G Garyu
(74) *Attorney, Agent, or Firm* — Cooper Legal Group LLC

(57) ABSTRACT

The present disclosure discloses an antimicrobial peptide Scyreprocin of *Scylla paramamosain* and a method thereof, wherein an amino acid sequence of the antimicrobial peptide Scyreprocin comprises a sequence shown in SEQ ID NO 01, and the antimicrobial peptide is expressed and purified by using genetic engineering technology. The recombinant antimicrobial peptide Scyreprocin has advantages of wide antimicrobial spectrum, good antimicrobial effect, and rapid germicidal rate, shows great application significance, and has good application in preparation of antimicrobial agents. The recombinant antimicrobial peptide Scyreprocin has no cytotoxicity to mouse hepatocytes AML12, human liver cells L02, and can be safely used for medical treatment or can be used as a feed composition.

3 Claims, 4 Drawing Sheets
Specification includes a Sequence Listing.

ANTIMICROBIAL PEPTIDE SCYREPROCIN OF *SCYLLA PARAMAMOSAIN* AND METHOD THEREOF

RELATED APPLICATIONS

This application is a continuation of International patent application PCT/CN2019/103237, filed on Aug. 29, 2019, which claims priority to Chinese patent application 201811394517.8, filed on Nov. 21, 2018. International patent application PCT/CN2019/103237 and Chinese patent application 201811394517.8 are incorporated herein by reference.

REFERENCE TO AN ELECTRONIC SEQUENCE LISTING

The contents of the electronic sequence listing (SequenceListing.txt; Size: 3,424 bytes; and Date of Creation: Apr. 14, 2021) is herein incorporated by reference.

FIELD OF THE DISCLOSURE

The present disclosure relates to bioengineering of natural products in crustaceans and in particular to antimicrobial peptide Scyreprocin of *Scylla paramamosain* and method thereof.

BACKGROUND OF THE DISCLOSURE

In order to meet the growth of food demand with the rapid growth of the world's population, in recent years, livestock, poultry, and aquaculture industries have developed rapidly, and a large number of antibiotics have been used against various pathogens in the industry. The application of antibiotics improves the utilization efficiency of feed and provides industrial economic benefits, but the abuse of antibiotics will also induce drug resistance of pathogenic microorganisms. The antibiotics remaining in soil, water, poultry, livestock, and aquatic products seriously affect the quality and safety of products and threaten human health. Therefore, looking for an efficient and green alternative to antibiotics has become a research hotspot in recent years. Antimicrobial peptides, which are safe, efficient, not easy to induce drug resistance of pathogenic microorganisms, residue free, and degradable in vivo and in vitro, are considered to be one of the ideal substitutes for antibiotics.

Antimicrobial peptide (AMP), also known as host defense peptide (HDP), is a kind of small molecular weight peptide with antimicrobial activity and is an important part of the innate immune defense system of animals. In 1972, Boman et al. first found AMPs and their immune functions in *Drosophila*. In 1981, Boman et al. successfully isolated two AMPs, *Cecropin* A and B, from *Hyalophora cecropin*. Since then, AMPs have been found in plants, insects, amphibians, aquatic products, mammals, and even some bacteria. So far, more than 2800 AMPs have been isolated, and more than 100 of them have been found in vertebrates. After more than 20 years of research, people have a deep understanding of the structure, function, and mechanism of the AMPs.

Natural AMPs are usually composed of 12 to 100 amino acid residues, most of which have the characteristics of strong alkalinity, thermal stability, and broad-spectrum antimicrobial activity. Natural AMPs not only kill bacteria, some fungi, protozoa, and drug-resistant bacteria, but also selectively kill tumor cells and inhibit the replication of hepatitis B virus. So far, researchers have found that AMPs can exert their functions through a variety of mechanisms, mainly including: ① most of the AMPs (such as *Cecropin*, CECP isolated from the small intestine of pigs, etc.) interact and destroy the membrane structure of microorganisms or cancer cells, resulting in a leakage of cellular contents, eventually leading to the death of tumor cells and microorganisms; ② some AMPs (such as fusion AMP DP1, RGD Tachyplesin et al.) kill tumor cells by inducing cell apoptosis; ③ human salivary AMP MUC7 and Thanatin kill microbes by attacking microbial mitochondria and inhibiting cell respiration; ④ a new antibacterial peptide $pvs4_{(13)}$ obtained by modification of Dermaseptin S4 can directly act on tumor cell chromatin through cell membrane; ⑤ *Cecropin* B, B1, and B3 not only induce pore formation in cancer cells, but also interfere with the normal function of microtubules, leading to dysfunction of cytoskeleton and organelles, and ultimately kill tumor cells; ⑥ human antibacterial peptide β2 defensin 3 can kill bacteria by inhibiting protein synthesis and cell wall formation, which eventually leads to perforation of the bacterial cell membrane and leakage of content, so as to achieve its bactericidal effect.

Most of the AMPs found above not only have strong antibacterial activity, with the development of research, the effects of AMPs against fungi, protozoa, viruses, and cancer cells has been revealed. Among them, *Cecropin* A, Magainin, Nisin, and other AMPs have been successively applied in medicine, food, and agriculture. As a new type of antibacterial material, AMPs have broad antibacterial spectrum and stable biological activity. AMPs kills microbes through physical action and destruction of the microbial membrane, making them less likely to induce drug resistance and a promising alternative to antibiotics. With in-depth studies on the structure and mechanism of AMPs, it could be expected that more new, efficient, broad-spectrum, and low-cytotoxic AMPs and their modified products will have a good application prospect in the fields of clinical medicine, feed additives, and livestock aquaculture.

BRIEF SUMMARY OF THE DISCLOSURE

A first object of the present disclosure is to provide an antimicrobial peptide Scyreprocin of *Scylla paramamosain*.

A second object of the present disclosure is to provide a method for applying the antimicrobial peptide Scyreprocin of *Scylla paramamosain*.

A first technical solution of the present disclosure is as follows.

An antimicrobial peptide Scyreprocin of *Scylla paramamosain*, wherein an amino acid sequence of the antimicrobial peptide Scyreprocin comprises a sequence of SEQ ID NO 01. The antimicrobial peptide Scyreprocin consists of 84 amino acids and is derived from *Scylla paramamosain*. The antimicrobial peptide Scyreprocin comprises 84 amino acids in total comprising 15 amino acid residues with positive charge and 7 amino acid residues with negative charge. According to an amino acid residue charge, an isoelectric point of the antimicrobial peptide is predicted to be 9.61. When the pH is 7.0, the antimicrobial peptide has 7 positive charges. An average hydrophilicity coefficient of the antibacterial peptide is −0.968, a water solubility of the antimicrobial peptide is relatively high, and the antimicrobial peptide is a cationic antimicrobial peptide with positive charge.

In an embodiment of the present disclosure, a nucleotide sequence of an open reading frame of the antimicrobial peptide Scyreprocin comprises a sequence of SEQ ID NO 02.

In an embodiment of the present disclosure, a molecular weight of the peptide Scyreprocin is 9107.258 Dalton, and a molecular formula of the antimicrobial peptide Scyreprocin is $C_{396}H_{636}N_{106}O_{127}S_4$.

The nucleotide sequence of SEQ ID NO 02 of the present disclosure can be easily mutated by conventional methods by those of ordinary skill in the art, such as directed evolution and point mutation methods. A nucleotide sequence artificially modified with 70% or higher of the identity of the nucleotide sequence of SEQ ID NO 02 isolated in the present disclosure is derived from the nucleotide sequence of the present disclosure and is equivalent to the sequence of the present disclosure, as long as the nucleotide sequence artificially modified is configured to encode the sequence of SEQ ID NO 01 and has a function of the sequence of SEQ ID NO 01.

The term "identity" as used herein refers to sequence similarity to a natural nucleic acid sequence (i.e., the nucleotide sequence of SEQ ID NO 02). "Identity" includes: a nucleotide sequence having 70% or higher, or 85% or higher, or 90% or higher, or 95% or higher of the identity to the nucleotide sequence (SEQ ID No 02) of the peptide of the amino acid sequence of SEQ ID NO 01 of the present disclosure. An identity can be evaluated by computer software.

The identity between two or more sequences can be expressed in percentage (%) by the computer software, which can be used to evaluate the identity between related sequences.

A second technical solution of the present disclosure is as follows.

An antimicrobial composition, wherein an effective component of the antimicrobial composition comprises the antimicrobial peptide Scyreprocin.

A third technical solution of the present disclosure is as follows.

A feed composition, wherein an effective component of the feed composition comprises the antimicrobial peptide Scyreprocin.

A fourth technical solution of the present disclosure is as follows.

An anti-mildew and antiseptic composition, wherein an effective component of the anti-mildew and antiseptic composition comprises the antimicrobial peptide Scyreprocin.

A fifth technical solution of the present disclosure is as follows.

A method for preparing of an antimicrobial composition comprising the antimicrobial peptide Scyreprocin.

A sixth technical solution of the present disclosure is as follows.

A method for preparing a feed composition comprising the antimicrobial peptide Scyreprocin.

A seventh technical solution of the present disclosure is as follows.

A method for preparing an anti-mildew and antiseptic composition comprising the antimicrobial peptide Scyreprocin.

Compared with the existing techniques, the present disclosure has the following advantages. 1. The Scyreprocin of the disclosure has remarkable antimicrobial effects on a variety of Gram-negative bacteria, Gram-positive bacteria, fungi, and molds. Among them, the minimum inhibition concentration for *Vibrio fluvialis* is 1-2 µM, for *Pseudomonas stutzeri* is 0.5-1 µM, and for *Staphylococcus aureus* is <0.5 µM. The minimum bactericidal concentration for a variety of Gram-negative bacteria and Gram-positive bacteria is 2-4 µM. In addition, the minimum inhibitory concentration for *Streptococcus albicans* is 2-4 µM, the minimum inhibitory concentration for *Cryptococcus neoformans* is 1-2 µM and the minimum bactericidal concentration is 8-16 µM, and the minimum inhibition concentration for *Aspergillus niger* is 4-8 µM. Therefore, compared with the known antimicrobial peptides identified in marine animals, the Scyreprocin of the disclosure has a wide antimicrobial spectrum, good antimicrobial activity and a rapid germicidal ability, showing great application value and good prospect in the preparation of antimicrobial agents.

2. The Scyreprocin of the disclosure has no cytotoxicity to mouse hepatocytes AML12, human liver cells L02, indicating that it can be safely used in drug treatment or as feed additive.

BRIEF DESCRIPTION OF THE DRAWINGS

FIG. 1 illustrates a sodium dodecyl sulphate-polyacrylamide gel (SDS-PAGE) electrophoresis showing a view of the recombinant Scyreprocin obtained by expression and purification, wherein M represents a protein marker 26616, 1 represents a total protein before expression induction, 2 represents a total protein after a 24-hour induction, 3 represents a supernatant obtained by ultrasonication, and 4 shows a purified recombinant Scyreprocin.

FIG. 2 illustrates a graph of a purification process of the recombinant Scyreprocin, wherein an arrow indicates a peak of the purified recombinant Scyreprocin.

DETAILED DESCRIPTION OF THE EMBODIMENTS

Figure 1:
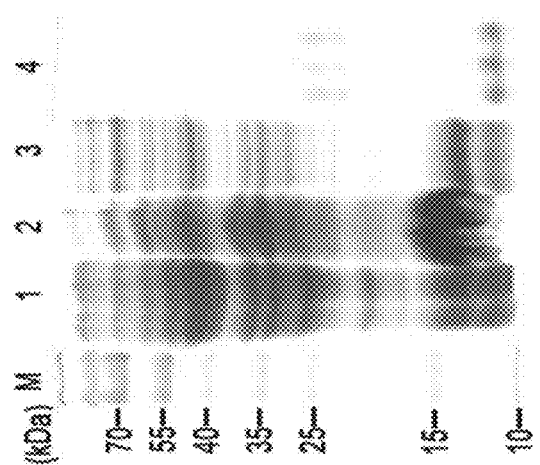
FIGS. 1 and 2 illustrates a resulting view of an antimicrobial peptide Scyreprocin of *Scylla paramamosain* obtained by a recombinant expression and purification of Embodiment 1 of the present disclosure.

The present disclosure will be further described below in combination with the accompanying drawings and embodiments.

A microbe of the following embodiments comprises *Escherichia coli, Escherichia coli* BL21, *Staphylococcus aureus, Vibrio fluvialis, Pseudomonas stutzeri, Micrococcus lysoleikticus, Candida albicans, Candida krusei, Candida tropicalis, Cryptococcus neoformans, Aspergillus niger,* etc., which were all purchased from China General Microbiological Culture Collection Center (CGMCC, belonging to Institute of Microbiology, Chinese Academy of Sciences). *Escherichia coli* MC1061 was purchased from ShenZhen Gene Power Tech. Co., Ltd., and *Pichia pastoris* GS115 was purchased from Invitrogen.

Embodiment 1: A Preparation of an Antimicrobial Peptide Scyreprocin of *Scylla paramamosain*

A sequence (i.e., a nucleotide sequence) of an open reading frame of an antimicrobial peptide Scyreprocin of *Scylla paramamosain* is as follows:

(SEQ ID NO 02)
ATGAAGGAAGACAGCAACATTCTAGACAAGACCGCCAAGATGACCAAAC

AGAACAAGGCCCTGCTCTTCACTGCAGGCGGCGCCGCGGCGTTCATGGC

AGGATACTACTACTATCACTGCAATTACAGAAATCCTGCACCCAAGAAA

AGTGGCAGTACTACTTCACAAGACAAGACTGATGCTCAGGCGGTTCAGT

CTATCCCCTCACCCAGTGGCAACAAGGGCAAAGAAAGCAAGGACCCAAA

AGTAAAATAA

A full-length of a cDNA sequence of a gene of the peptide Scyreprocin was obtained and verified by Rapid Amplification of cDNA ends (RACE). The open reading frame of the gene of the peptide Scyreprocin is 255 bp (comprising a termination codon TAA), and a GenBank Accession number is MH488960.

According to the cDNA sequence of the gene of the peptide Scyreprocin, the gene specific primers were designed and repeatedly verified by the RACE method (Table 1).

TABLE 1

A primer list for Scyreprocin sequence amplification

| Primer name | Sequence 5'-3' |
| --- | --- |
| Scyreprocin 3'-1 | GCAAAGAAAGCAAGGACCCAAAA (SEQ ID NO 03) |
| Scyreprocin 3'-2 | TGCTCAGGCGGTTCAGTCTATCC (SEQ ID NO 04) |
| Scyreprocin 3'-3 | ACAAGACCGCCAAGATGACCAAA (SEQ ID NO 05) |
| Scyreprocin 5'-1 | TCTGTTTGGTCATCTTGGCGGTCTT (SEQ ID NO 06) |
| Scyreprocin 5'-2 | CCACTGGGTGAGGGGATAGACTGAA (SEQ ID NO 07) |
| Scyreprocin 5'-3 | ACTTTTGGGTCCTTGCTTTCTTTGC (SEQ ID NO 08) |
| Scyreprocin full-length F | TTCACGCCACTCAGTACAAATCTA (SEQ ID NO 09) |
| Scyreprocin full-length R | CAAACATAAGTAAAGCTGAAGGTA (SEQ ID NO 10) |
| 5'RACE Outer Primer | CATGGCTACATGCTGACAGCCTA (SEQ ID NO 11) |
| 5'RACE Inner Primer | CGCGGATCCACAGCCTACTGATGATCAGTCGATG (SEQ ID NO 12) |
| 3'RACE Outer Primer | TACCGTCGTTCCACTAGTGATTT (SEQ ID NO 13) |
| 3'RACE Inner Primer | CGCGGATCCTCCACTAGTGATTTCACTATAGG (SEQ ID NO 14) |

A noncoding sequence of the gene of the peptide Scyreprocin of *Scylla paramamosain* was amplified by the RACE method (i.e., a 5'UTR amplification method):

The cDNA prepared by method RACE (i.e., by the applicant) was taken as a polymerase chain reaction (PCR) template, and a specific reaction system is as follows:

1) Outer PCR reaction:

| | |
| --- | --- |
| cDNA | 2 μL |
| 10 × LA PCR Buffer II (Mg$^{2+}$ plus) | 5 μL |

-continued

| | |
| --- | --- |
| dNTP Mixture (2.5 mM each) | 8 μL |
| 5' RACE Outer Primer (10 μM) | 2 μL |
| Scyreprocin 5'-3 (10 μM) | 2 μL |
| LA Taq (5 U/μL) | 0.25 μL |
| Milli-Q water | 30.75 μL |
| Total reaction volume | 50 μL |

A reaction process is as follows:
1) Pre-denaturizing at 95° C. for 3 minutes;
2) Denaturizing at 95° C. for 30 seconds, annealing at 60° C. for 30 seconds, and elongating at 72° C. for 2 minutes as a cycle, and cycling for 20 times in total;
3) Elongating at 72° C. for 10 minutes; and
4) Stopping at 4° C. to obtain a first round PCR product.

The first round PCR product was diluted for 50-100 times to obtain a diluted outer PCR reaction solution, and the diluted outer PCR reaction solution was then used as a template for nested PCR amplification. A reaction system was as follows:

② Inner PCR Reaction:

| | |
| --- | --- |
| Diluted outer PCR reaction solution | 2 μL |
| 10 × LA PCR Buffer II (Mg$^{2+}$ plus) | 5 μL |
| dNTP Mixture (2.5 mM each) | 8 μL |

-continued

| | |
| --- | --- |
| 5' RACE Outer Primer (10 μM) | 2 μL |
| Scyreprocin 5'-2 (10 μM) | 2 μL |
| LA Taq (5 U/μL) | 0.25 μL |
| Milli-Q water | 30.75 μL |
| Total reaction volume | 50 μL |

The aforementioned reactants were well mixed to carry out a PCR reaction. A reaction process is as follows:

1) Pre-denaturizing at 95° C. for 5 minutes;
2) Denaturizing at 95° C. for 30 seconds, annealing at 60° C. for 30 seconds, and elongating at 72° C. for 2 minutes as a circle, and cycling for 30 times in total;
3) Elongating at 72° C. for 10 minutes; and
4) Stopping at 4° C. to obtain amplification products.

A 3'UTR amplification method of the gene of the peptide Scyreprocin is similar to the 5' UTR amplification method. The amplification products were sequenced and were then spliced to obtain the full length of the cDNA sequence of the gene of the peptide Scyreprocin. Proper primers were designed, the cDNA sequence of *Scylla paramamosain* was taken as a template, and a full length of the gene of the peptide Scyreprocin obtained by the splicing was verified. A PCR reaction system is as follows:

| | |
|---|---|
| cDNA | 2 µL |
| 10 × LA PCR Buffer II (Mg$^{2+}$ plus) | 5 µL |
| dNTP Mixture (2.5 mM each) | 8 µL |
| Scyreprocin full-length F (10 µM) | 2 µL |
| Scyreprocin full-length R(10 µM) | 2 µL |
| LA Taq (5 U/µL) | 0.25 µL |
| Milli-Q water | 30.75 µL |
| Total reaction volume | 50 µL |

The aforementioned reactants were well mixed to carry out a PCR reaction. A reaction process is as follows:
1) Pre-denaturizing at 95° C. for 5 minutes;
2) Denaturizing at 95° C. for 30 seconds, annealing at 55° C. for 30 seconds, and elongating at 72° C. for 1 minute as a cycle, and cycling for 30 times in total;
3) Elongating at 72° C. for 5 min; and
4) Stopping at 4° C.

The gene of the peptide Scyreprocin is derived from *Scylla paramamosain*, and an amino acid sequence of the peptide Scyreprocin is as follows:

(SEQ ID NO 01)
MKEDSNILDKTAKMTKQNKALLFTAGGAAAFMAGYYYYHCNYRNPAPKKS

GSTTSQDKTDAQAVQSIPSPSGNKGKESKDPKVK.

A molecular formula of the peptide Scyreprocin is $C_{396}H_{636}N_{106}O_{127}S_4$, and a molecular weight of the peptide Scyreprocin is 9107.258 Dalton. As predicted by SignalP4.1 software, there is no signal peptide in the peptide Scyreprocin, and there are 84 amino acids in total comprising 15 amino acid residues with positive charge and 7 amino acid residues with negative charge. According to an amino acid residue charge, an isoelectric point of the peptide Scyreprocin is predicted to be 9.61. An average hydrophilicity coefficient of the peptide Scyreprocin is −0.968, a water solubility of the peptide Scyreprocin is relatively high. When the pH is 7.0, a net charge of the peptide Scyreprocin is +7, indicating it a cationic peptide.

Figure 2:
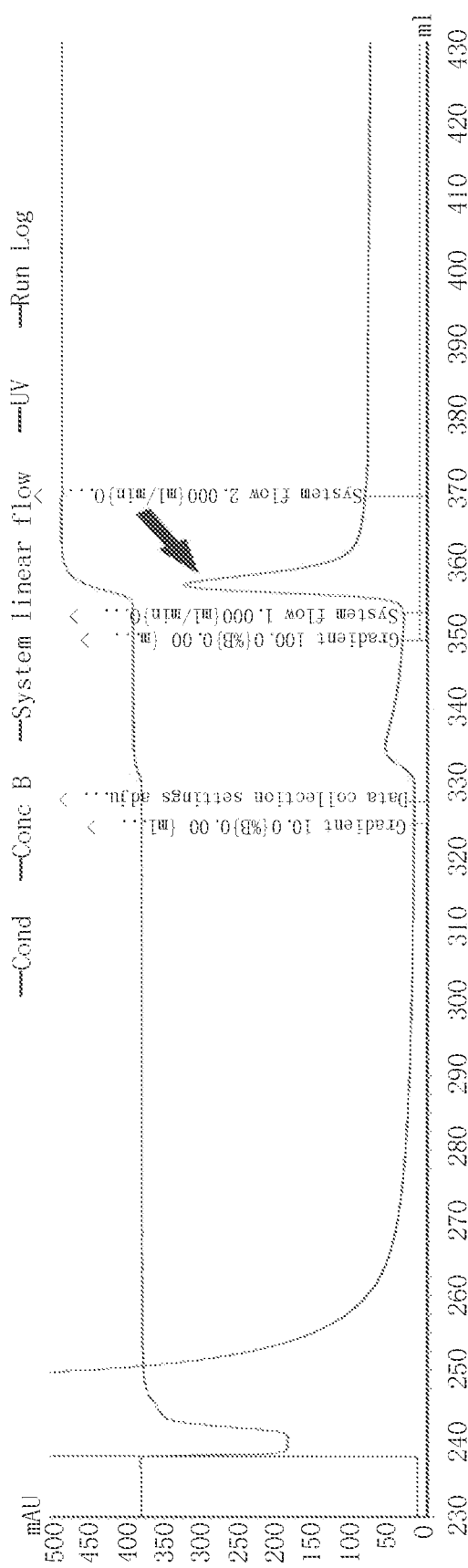

A recombinant product of Scyreprocin with a purity of more than 85% was obtained by a gene engineering expression technology. In this embodiment, the antimicrobial peptide Scyreprocin of *Scylla paramamosain* was expressed and purified by the gene engineering technology in a laboratory (the results are shown in FIGS. 1 and 2).

Embodiment 2: An Expression Product Comprising the Antibacterial Peptide Scyreprocin of *Scylla paramamosain* was Obtained by Gene Engineering (a) The cDNA template of *Scylla paramamosain* was cloned to obtain the open reading frame sequence of the antimicrobial peptide Scyreprocin of *Scylla paramamosain*, and the open reading frame was cloned and recombined to a vector pET28a to obtain a recombinant vector. The recombinant vector with a correct open reading frame was verified by base sequencing and was transferred into *Escherichia coli* BL21 to obtain a recombinant expression strain configured to express the antimicrobial peptide Scyreprocin of *Scylla paramamosain* with a His tag.

(b) A clone of the recombinant expression strain was selected and cultured in a liquid medium Luria-Bertani (LB) at 37° C. for 10-14 hours at a speed of 180 revolutions per minute (RPM) in a shake flask, then transferred to a liquid medium LB comprising 0.5% glucose with a ratio of 1:1000, and was then cultured until $OD_{600}$=0.3. Isopropyl β-d-1-thiogalactopyranoside (IPTG) was added to a final concentration of 0.5 mM (mmol/L) to induce expression, and the strain was cultured at 16° C. for 24 hours at a speed of 160 RPM. The strain was collected by centrifugation, and suspended with a 50 mM phosphate buffer (pH 8.0) at a volume ratio of 1:10.

(c) Phenylmethylsulfonyl fluoride (PMSF) was added to the suspensions to inhibit protease activity. The strain was ultrasonicated and centrifuged at a speed of 12000 RPM for 30 minutes to obtain a strain lysate supernatant comprising the recombinant Scyreprocin. After the strain lysate supernatant was filtered by a 0.22 µM filter membrane, recombinant Scyreprocin with the His tag was purified by a Ni column affinity chromatography.

(d) The recombinant Scyreprocin with the His tag (i.e., a protein purification solution) was dialyzed in a dialysate (50 mM Tris HCl, 50 mM NaCl, pH 8.0) for 16-18 hours to remove imidazole from the protein purification solution, and the protein purification solution was transferred to Milli-Q water and was then dialyzed for 10-12 hours.

(e) The dialyzed recombinant Scyreprocin was concentrated by ultrafiltration through an ultrafiltration tube, and a protein concentration was measured by a Bradford method. The concentrated recombinant Scyreprocin (i.e., the purified protein) was stored at −80° C. before use. The purified protein was detected by a denaturing gradient gel electrophoresis (i.e., an SDS-PAGE electrophoresis) and mass spectrometry, and the purified protein was identified as the antimicrobial peptide Scyreprocin of *Scylla paramamosain*.

Embodiment 3: A MIC (Minimum Inhibition Concentration) of the Recombinant Scyreprocin was Detected (a) The preserved *Escherichia coli*, *Escherichia coli* MC1061, *Pseudomonas stutzeri*, *Pseudomonas hydrophila*, *Staphylococcus aureus*, and *Micrococcus lysoleikticus* were streaked on a nutrient broth plate, the *Vibrio fluvialis* was streaked on a marine broth 2216E plate. The microbes were cultured at their corresponding optimum temperature for 12-16 hours. *Candida albicans*, *Pichia pastoris*, *Candida krusei*, *Candida tropicalis*, and *Cryptococcus neoformans* were streaked on yeast extract peptone glycerol (YPG) plates and cultured at 28° C. for 1-2 weeks; *Aspergillus niger* spores were coated on a plate potato dextrose agar (PDA) and cultured at 28° C. for 3-7 days. Colonies of each plate were selected and inoculated on a slant surface of the corresponding medium. For bacteria, the colonies were cultured for 10-16 hours. For fungi, the colonies were cultured for 1-3 days. For molds, the colonies were cultured for 3-7 days. The slant surface of the corresponding medium was washed with a 10 mM phosphate buffer (pH 7.4). Bacteria were diluted liquid medium Mueller-Hinton (MH)

(diluted to $OD_{600}$=0.003). *Vibrio* were diluted marine broth 2216E (diluted to $OD_{600}$=0.0006). Yeasts were diluted by yeast extract peptone dextrose (YPD) (diluted to $OD_{600}$=0.00067). Molds were diluted by PDA (diluted to a spore concentration of $5×10^4$ spores/mL) (Embodiment 4 describes a specific operation). The prepared microbe solutions were used within 20 minutes.

(b) The recombinant Scyreprocin was filtered by a 0.22 μM filter film. A protein concentration was then assayed by a Bradford method, and the protein concentration was diluted to 0.5, 1, 2, 4, 8, 16, and 32 μM. The antimicrobial peptide was stored at 4° C.

(c) A minimum inhibitory concentration test was carried out on 96-well plates. Each microbe to be tested comprised a blank control group, a negative control group, and a test group. In accordance with the following operations, each group of the blank control group, the negative control group, and the test group comprised 3 parallel samples.

The negative control group: 50 μL sterile ultra-pure water and 50 μL microbe suspension were added.

The blank control group: 50 μL protein sample to be tested and 50 μL phosphate buffer were added.

The test group: 50 μL protein sample to be tested and 50 μL microbe suspension were added.

For bacteria, the 96-well plates were placed at an optimum temperature for each microbe and cultured for 18-24 hours, and results were observed.

For fungi, *vibrio*, and molds, the 96-well plates were placed at 28° C. for 1-2 days and results were observed.

The liquid medium in the test group where the growth of bacteria was not observed by naked eyes was evenly mixed to obtain a mixture medium, 2 μL of the mixture medium was inoculated to a corresponding plate and cultured at the optimum growth temperature for 24-48 hours. Minimum bactericidal concentration (MBC) results were observed.

MIC and MBC results of the recombinant Scyreprocin are shown in Table 2.

TABLE 2

Determination of antimicrobial activity of Scyreprocin

| Microorganism | CGMCC No. | MIC(μM) | MBC(μM) |
|---|---|---|---|
| Gram-negative bacteria | | | |
| *Escherichia coli* | 1.2389 | 2-4 | >15 |
| *Pseudomonas stutzeri* | 1.1803 | 0.5-1 | 1-2 |
| *Vibrio fluvialis* | 1.1609 | 1-2 | 2-4 |
| *Escherichia coli* MC1061 | — | 2-4 | 4-8 |
| Gram-positive bacteria | | | |
| *Staphylococcus aureus* | 1.363 | <0.5 | 2-4 |
| *Micrococcus lysoleikticus* | 1.0634 | <0.5 | 1-2 |
| *Bacillus subtilis* | 1.108 | 1-2 | 4-8 |
| Fungi | | | |
| *Candida krusei* | 2.1857 | 8-16 | >32 |
| *Candida albicans* | 2.2411 | 2-4 | 16-32 |
| *Cryptococcus neoformans* | 2.1563 | 1-2 | 8-16 |
| *Candida tropicalis* | 2.1975 | 16-32 | >32 |
| *Pichia pastoris* (GS115) 2.2238 | Invitrogen | 4-8 | >30 |
| *Aspergillus niger* | 3.0316 | 4-8 | >32 |

Note:
MIC: minimum inhibitory concentration (μM) and a-b represents MIC, wherein a represents a highest concentration of the recombinant Scyreprocin in which microbial growth was observed by naked eyes, and b represents a lowest concentration of the recombinant Scyreprocin in which no microbe growth was observed.
MBC: minimum bactericidal concentration (μM), a minimum concentration of the recombinant Scyreprocin configured to kill 99.9% of bacteria.

Embodiment 4: Spore Germination of *Aspergillus niger* Inhibited by the Recombinant Scyreprocin was Detected (a) A preserved *Aspergillus niger* was coated on a plate PDA and was cultured at 28° C. for 3-7 days to obtain spores.

(b) The spores were collected from the plate PDA, inoculated on a slant surface PDA, and cultured at 28° C. for 3-7 days. The slant surface was washed with 10 mM phosphate buffer (pH 7.4), the hypha were removed by filtration with a cell strainer (an aperture of the cell strainer is 100 nm), and the fungal spores (i.e., a spore suspension) were collected. A PDA liquid medium and 10 mM phosphate buffer with a ratio of 1:1 were used, and a spore concentration was adjusted to $5×10^4$ spores/mL.

(c) The recombinant Scyreprocin was filtered with a 0.22 μM filter membrane, diluted to a concentration of 0.5, 1, 2, 4, 8, 16, 32 μM, and placed on ice for use.

(d) 96-well plates were set with a positive control group and a test group as follows, and each group comprised three parallel samples.

The positive control group: 50 μL spore suspension and 50 μL 10 mM phosphate buffer were added.

The test group: 50 μL spore suspension and 50 μL recombinant Scyreprocin were added.

Figure 3:
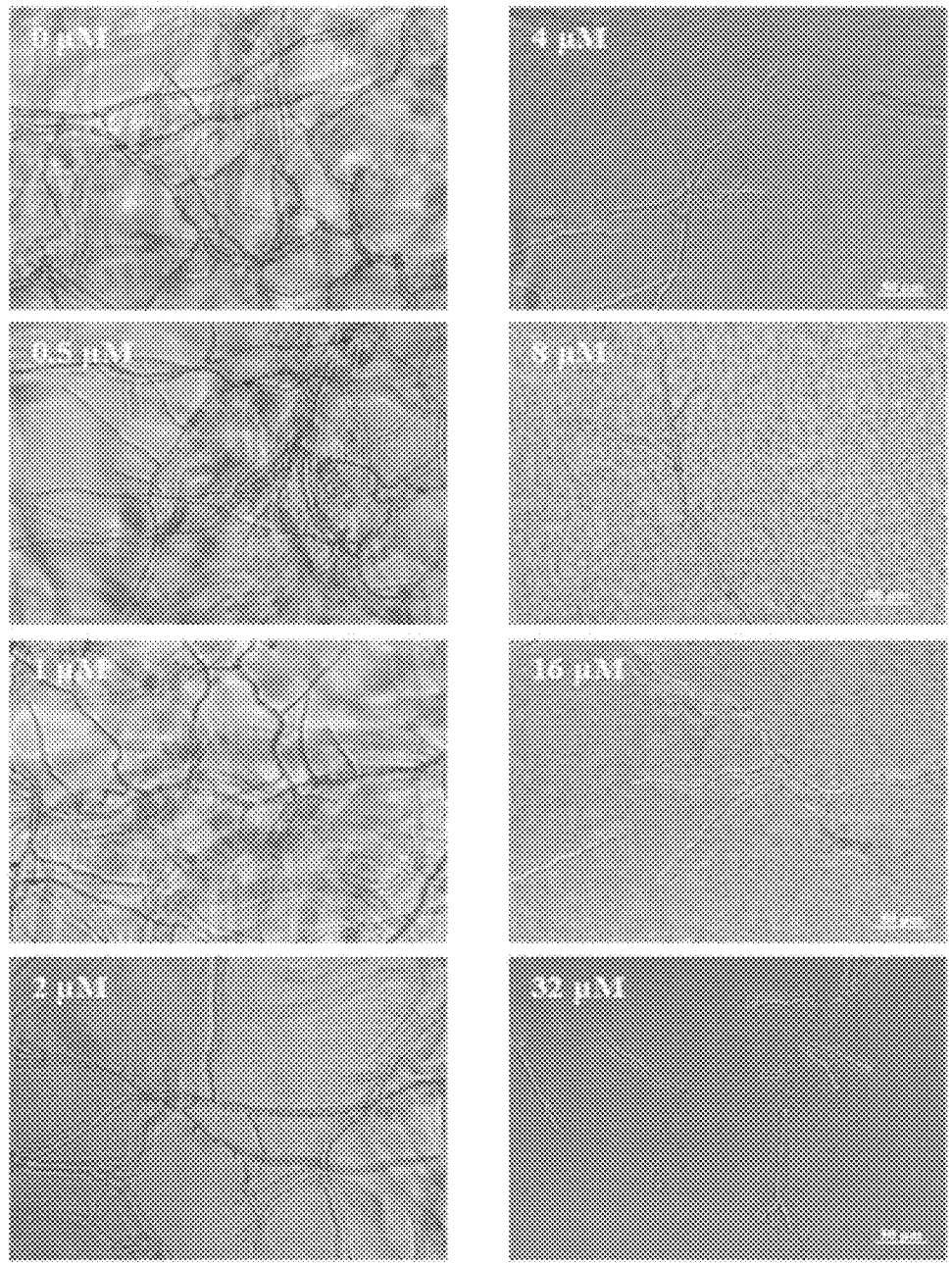
FIG. 3 illustrates a resulting view of a spore germination of *Aspergillus niger* inhibited by the recombinant Scyreprocin.
Figure 4A:
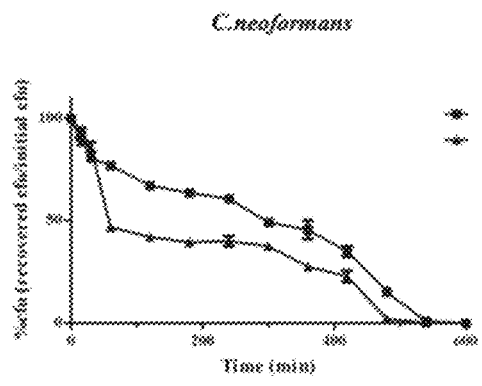
FIGS. 4A-4D illustrate a bactericidal kinetic curve of the recombinant Scyreprocin against *Cryptococcus neoformans, Candida albicans, Pseudomonas schneideri,* and *Micrococcus lysoleikticus,* respectively. An abscissa represents time (min), and an ordinate represents a percentage of survival colonies relative to original colonies.
Figure 4C:
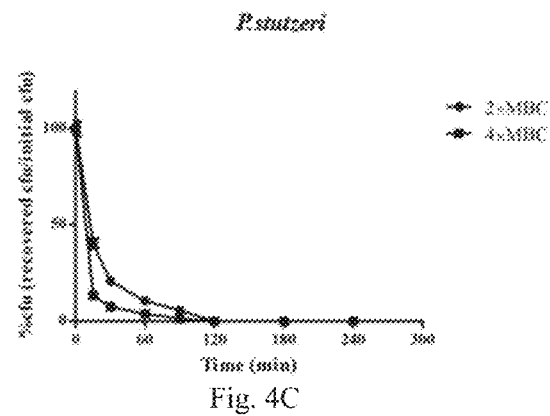
Figure 4B:
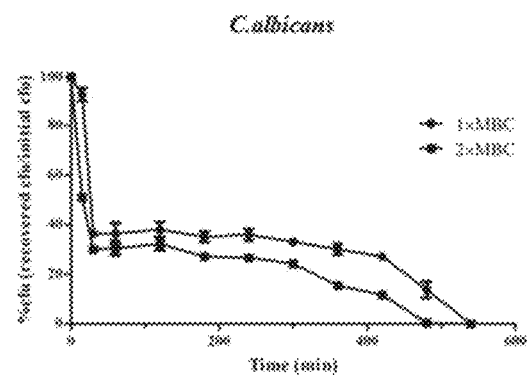
Figure 4D:
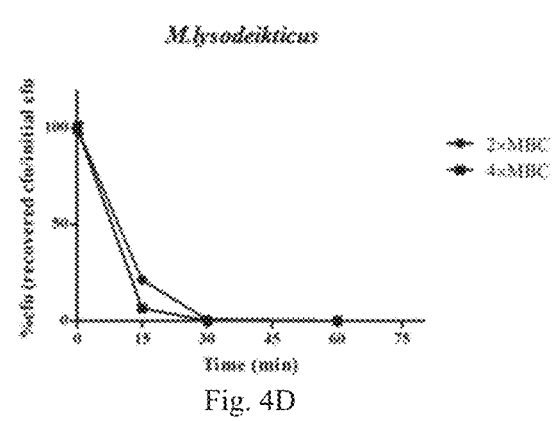

The 96-well plates were cultured in a 28° C. incubator for 24 hours, and spore germination of *Aspergillus niger* was observed by an optical microscope. Referring to FIG. 3, as a result, the 4 M recombinant Scyreprocin significantly inhibited the spore germination of *Aspergillus niger*.

Embodiment 5: Bactericidal Kinetic Curve of the Recombinant Scyreprocin

In this embodiment, a Gram-negative bacterium (*Pseudomonas stutzeri*), a Gram-positive bacterium (*Micrococcus lysoleikticus*), and two fungi (*Candida albicans* and *Cryptococcus neoformans*) were selected as bacteria to be tested, and a germicidal kinetic curve of the recombinant Scyreprocin was generated.

(a) *Pseudomonas stutzeri* and *Micrococcus lysoleikticus* were maintained on nutrient broth plates. *Candida albicans* and *Cryptococcus neoformans* were maintained on YPD plates. The aforementioned microbes were cultured at an optimum temperature.

(b) Colonies were selected from the plates (i.e., the nutrient broth plates or the YPD plates), were inoculated on a slant surface, and cultured. The slant surface was washed with a 10 mM phosphate buffer (pH 7.4) to obtain microbial suspensions. A concentration of the microbial suspensions was adjusted to $OD_{600}$=$3.3×10^4$ cfu/mL with a mixed medium comprising a liquid medium MH (or a liquid medium YPD) and a 10 mM phosphate buffer with a ratio of 2:3.

(c) The recombinant Scyreprocin was filtered by a 0.22 m filter membrane, diluted to 0.5, 1, 2, 4, 8, 16, 32 μM, and placed on ice for use.

(d) 96-well plates were set with a positive control group and a test group as follows, and each group comprised three parallel samples.

The positive control group: 100 μL microbe suspension and 100 μL 10 mM phosphate buffer were added.

The test group: 100 μL microbe suspension and 100 μL recombinant Scyreprocin were added.

The 96-well plates were cultured at 28° C. A proper amount of culture medium was sampled after 0, 15, 30, 60, 90, 120, 180, and 240 minutes, diluted, and coated on nutrient broth plates or YPD plates. The 96-well plates were cultured and the number of clones on each plate was counted. A bactericidal kinetics curve was generated (referring to FIG. 4) due to statistical analysis. As a result, the recombinant Scyreprocin with 2×MBC killed 50% of *Cryptococcus neoformans* and *Candida albicans* in 100 minutes, and a fungicidal index reached 100% in 500 minutes. After the recombinant Scyreprocin with 2×MBC acted on *Micrococcus* lysozyme for 60 minutes, a bactericidal index reached 100%. After the recombinant Scyreprocin with 2×MBC acted on the *Pseudomonas stutzeri* for 180 minutes, a bactericidal index reached 100%.

Embodiment 6: The Effect of the Recombinant Scyreprocin on the Proliferation of Animal Cell Line In this example, human liver cells L02 and mouse hepatocyte AML12 were selected as test cell lines, and the anti-proliferation effect against different cells of recombinant Scyreprocin.

(a) The human liver cells L02 and the mouse hepatocyte AML12 were maintained in a corresponding cell culture medium, digested with trypsin comprising ethylenediaminetetraacetic acid (EDTA), and resuspended in the corresponding cell culture medium. The cell density was adjusted, and $2 \times 10^5$ cells were inoculated in each well of a 96-well plate and cultured overnight at 37° C. in 5% $CO_2$.

(b) The medium was removed, and the recombinant Scyreprocin was diluted to 0.5, 1, 2, 4, 8, and 16 μM with the corresponding cell culture medium. The corresponding cell culture medium was used as a control group, and each group comprised three parallel samples.

Figure 5:
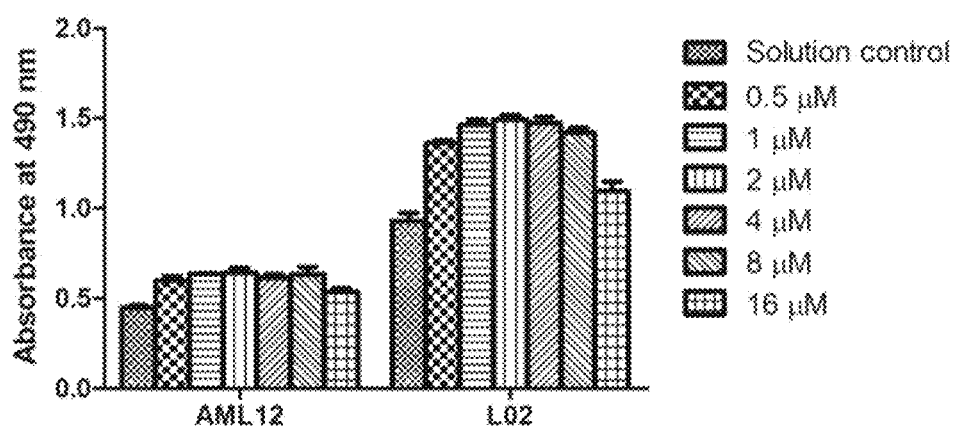
FIG. 5 illustrates a resulting view of a proliferation effect of the recombinant Scyreprocin by a method MTS ([3-(4, 5-dimethylthiazol-2-yl)-5-(3-carboxymethoxyphenyl)-2-(4-sulfophenyl)-2H-tetrazolium]) against mouse hepatocytes (AML12) and human liver cells (L02).

The 96-well plate was placed at 37° C. in 5% $CO_2$ for 48 hours, then a 20 μL MTS reagent ([3-(4,5-dimethylthiazol-2-yl)-5-(3-carboxymethoxyphenyl)-2-(4-sulfophenyl)-2H-tetrazolium]) was added to each well, and incubated for 2 hours. The absorption value at 490 nm was measured by a microplate reader. Referring to FIG. 5, as a result, the recombinant Scyreprocin had no inhibitory effect on the growth of the mouse hepatocyte AML12 and human liver cells L02.

The aforementioned embodiments are merely some embodiments of the present disclosure, and the scope of the disclosure is not limited thereto. Thus, it is intended that the present disclosure cover any modifications and variations of the presently presented embodiments provided they are made without departing from the appended claims and the specification of the present disclosure.

What is claimed is:

1. A method for preparing an antimicrobial composition to be used to inhibit growth of microorganisms, wherein the method comprises recombination expression and purification of an antimicrobial peptide Scyreprocin of *Scylla paramamosain* with a His tag, wherein an amino acid sequence of the antimicrobial peptide Scyreprocin consists of SEQ ID NO: 01, and wherein the recombination expression and purification comprises:

cloning an open reading frame of the antimicrobial peptide Scyreprocin of *Scylla paramamosain* and constructing into a vector pET28a to obtain a recombinant vector; and transferring the recombinant vector into *Escherichia coli* BL21 to obtain a recombinant expression strain configured to express the antimicrobial peptide Scyreprocin of *Scylla paramamosain* with a protein purification solution.

2. The method according to claim 1, wherein the antimicrobial composition is a feed composition.

3. The method according to claim 1, wherein the antimicrobial composition is an anti-mildew and antiseptic composition.

* * * * *

SEQUENCE LISTING

```
<160> NUMBER OF SEQ ID NOS: 14

<210> SEQ ID NO 1
<211> LENGTH: 84
<212> TYPE: PRT
<213> ORGANISM: Scylla paramamosain

<400> SEQUENCE: 1

Met Lys Glu Asp Ser Asn Ile Leu Asp Lys Thr Ala Lys Met Thr Lys
1               5                   10                  15

Gln Asn Lys Ala Leu Leu Phe Thr Ala Gly Gly Ala Ala Ala Phe Met
            20                  25                  30

Ala Gly Tyr Tyr Tyr Tyr His Cys Asn Tyr Arg Asn Pro Ala Pro Lys
        35                  40                  45

Lys Ser Gly Ser Thr Thr Ser Gln Asp Lys Thr Asp Ala Gln Ala Val
    50                  55                  60

Gln Ser Ile Pro Ser Pro Ser Gly Asn Lys Gly Lys Glu Ser Lys Asp
65                  70                  75                  80

Pro Lys Val Lys

<210> SEQ ID NO 2
<211> LENGTH: 255
<212> TYPE: DNA
<213> ORGANISM: Scylla paramamosain

<400> SEQUENCE: 2
atgaaggaag acagcaacat tctagacaag accgccaaga tgaccaaaca gaacaaggcc        60
ctgctcttca ctgcaggcgg cgccgcggcg ttcatggcag gatactacta ctatcactgc       120
aattacagaa atcctgcacc caagaaaagt ggcagtacta cttcacaaga caagactgat       180
gctcaggcgg ttcagtctat ccctcaccc agtggcaaca agggcaaaga aagcaaggac       240
ccaaaagtaa aataa                                                         255

<210> SEQ ID NO 3
```

```
<211> LENGTH: 23
<212> TYPE: DNA
<213> ORGANISM: Artificial Sequence
<220> FEATURE:
<223> OTHER INFORMATION: Synthetic

<400> SEQUENCE: 3
gcaaagaaag caaggaccca aaa                                          23

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4
tgctcaggcg gttcagtcta tcc                                          23

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
acaagaccgc caagatgacc aaa                                          23

<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
tctgtttggt catcttggcg gtctt                                        25

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
ccactgggtg aggggataga ctgaa                                        25

<210> SEQ ID NO 8
<211> LENGTH: 25
<212> TYPE: DNA
<213> ORGANISM: Artificial Sequence
<220> FEATURE:
<223> OTHER INFORMATION: Synthetic

<400> SEQUENCE: 8
acttttgggt ccttgctttc tttgc                                        25

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
```

-continued

<210> SEQ ID NO 9 (continued)

ttcacgccac tcagtacaaa tcta                                              24

<210> SEQ ID NO 10
<211> LENGTH: 24
<212> TYPE: DNA
<213> ORGANISM: Artificial Sequence
<220> FEATURE:
<223> OTHER INFORMATION: Synthetic

<400> SEQUENCE: 10
caaacataag taaagctgaa ggta                                              24

<210> SEQ ID NO 11
<211> LENGTH: 23
<212> TYPE: DNA
<213> ORGANISM: Artificial Sequence
<220> FEATURE:
<223> OTHER INFORMATION: Synthetic

<400> SEQUENCE: 11
catggctaca tgctgacagc cta                                               23

<210> SEQ ID NO 12
<211> LENGTH: 34
<212> TYPE: DNA
<213> ORGANISM: Artificial Sequence
<220> FEATURE:
<223> OTHER INFORMATION: Synthetic

<400> SEQUENCE: 12
cgcggatcca cagcctactg atgatcagtc gatg                                   34

<210> SEQ ID NO 13
<211> LENGTH: 23
<212> TYPE: DNA
<213> ORGANISM: Artificial Sequence
<220> FEATURE:
<223> OTHER INFORMATION: Synthetic

<400> SEQUENCE: 13
taccgtcgtt ccactagtga ttt                                               23

<210> SEQ ID NO 14
<211> LENGTH: 32
<212> TYPE: DNA
<213> ORGANISM: Artificial Sequence
<220> FEATURE:
<223> OTHER INFORMATION: Synthetic

<400> SEQUENCE: 14
cgcggatcct ccactagtga tttcactata gg                                     32